United States Patent [19]

Gilman

[11] Patent Number: 5,060,642
[45] Date of Patent: Oct. 29, 1991

[54] WOUND DRESSING WITH AIR PERMEABLE BACTERIA IMPERMEABLE RESERVOIR

[76] Inventor: Thomas H. Gilman, 2156 Sunrise Dr., Appleton, Wis. 54915

[21] Appl. No.: 461,598

[22] Filed: Jan. 5, 1990

[51] Int. Cl.$^5$ ............... A61F 13/00; A61F 15/00
[52] U.S. Cl. .................... 128/155; 128/156; 128/888; 604/385.1
[58] Field of Search ............ 128/155, 156, 888; 604/304, 307, 385.1

[56] References Cited

U.S. PATENT DOCUMENTS

| | | | |
|---|---|---|---|
| 2,443,140 | 6/1948 | Larsen | 128/888 |
| 3,814,097 | 6/1974 | Ganderton et al. | 604/304 |
| 3,965,906 | 6/1976 | Karami | 128/156 |
| 4,399,816 | 8/1983 | Spangler | 128/888 |
| 4,676,785 | 6/1987 | Battista | 604/385.1 |

FOREIGN PATENT DOCUMENTS 0842617 7/1960 United Kingdom ............... 128/155

*Primary Examiner*—Randall L. Green
*Assistant Examiner*—Paul Prebilic
*Attorney, Agent, or Firm*—Alvin Isaacs

[57] ABSTRACT

Novel wound dressing having a sealed absorbent fabric design and structure wherein an absorbent fabric providing a reservoir for retaining wound exudate is contained between a bottom liquid-permeable sheet material permitting the wicking or diffusion of wound exudate and an outer cover characterized as being a bacterial barrier, at least a portion of the outer cover also being air-permeable for permitting egress of air from the interstices or voids in the fabric reservoir to the ambient atmosphere.

10 Claims, 1 Drawing Sheet

WOUND DRESSING WITH AIR PERMEABLE BACTERIA IMPERMEABLE RESERVOIR

BACKGROUND OF THE INVENTION

This invention relates to novel wound dressings and, more particularly, to wound dressings such as those applied after surgery for the wicking and reservoir or retention of wound fluid.

The prior art is of course replete with references to various types of wound dressings from the simplest of absorbent pads to the more sophisticated designs additionally providing a barrier to external contaminants. As an illustration of the latter, mention may be made of those described and claimed in U.S. Pat. No. 4,499,896 which may additionally include an absorbent pad.

The task of the present invention, simply stated, is to provide a new and improved absorbent fabric structure for wound treatment which not only provides a complete barrier to bacteria and other external contaminants but also optimizes the wicking and amount of wound fluid which can be retained in the volume provided by the absorbent fabric, thereby minimizing the frequency of dressing changes required in the wound treatment procedure.

DESCRIPTION OF THE INVENTION

In accordance with the present invention, this task is solved in an efficient, cost-effective and elegant manner by providing a sealed absorbent fabric design and structure wherein the absorbent fabric providing a reservoir for retaining wound exudate is contained between a thin bottom liquid-permeable film or sheet material permitting the wicking or diffusion of exudate from the wound to the absorbent fabric fluid reservoir contained therein; and an outer cover characterized as being a bacterial barrier, at least a portion of the outer cover also being air-permeable for egress of air from the interstices or voids in the fabric reservoir to the ambient atmosphere.

In accordance with this invention, the novel sealed absorbent fabric structure of this invention is designed and adapted for placement directly on the wound.

My copending application, Ser. No. 461,588 filed concurrently describes and claims a modification thereof wherein the sealed fabric structure is employed for use in combination with a dressing of the type described in my copending application, Ser. No. 337,591 filed Apr. 13, 1989.

DETAILED DESCRIPTION OF THE INVENTION

Figure 1:
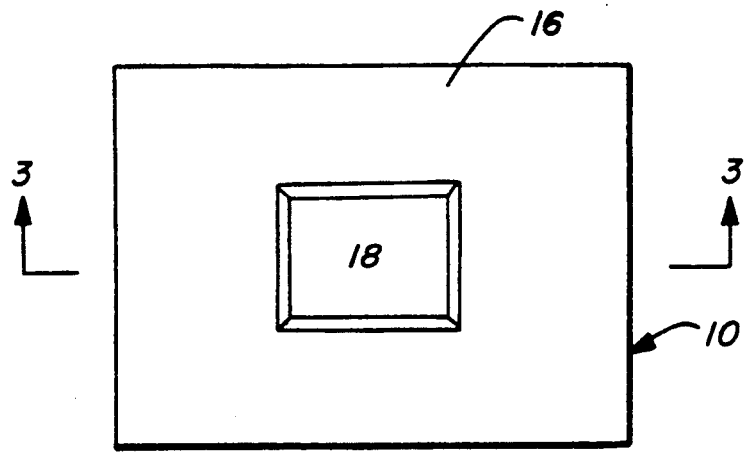
FIG. 1 is a top plan view of the novel sealed fabric wound dressing of this invention.
Figure 2:
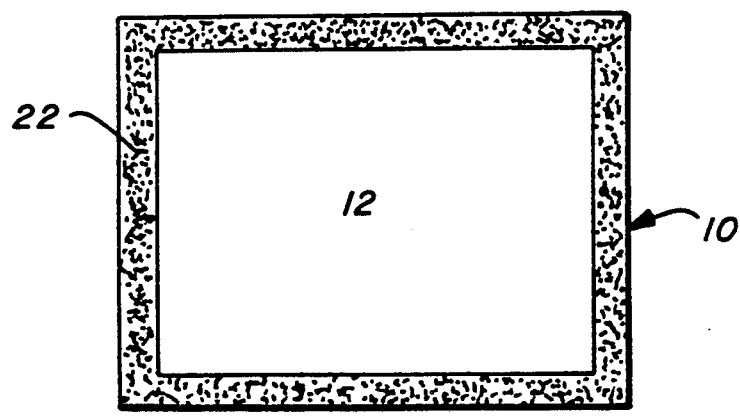
FIG. 2 is a bottom plan view of the dressing of FIG. 1.
Figure 3:
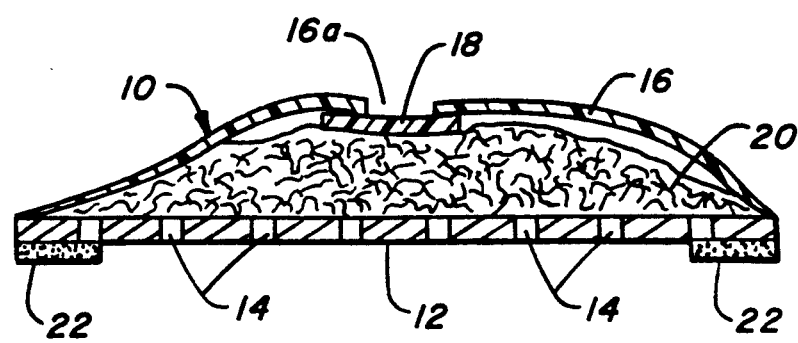
FIG. 3 is a sectional view taken substantially as indicated along the line 3—3 of FIG. 1 with the thicknesses exaggerated for purposes of illustration.

The desirability of removing exudate from the healing wound surface is of course well documented. Apart from the messiness of the exudate escaping from the confines of the dressing or diffusing laterally to cause the adhesive retaining the dressing to lose its aggressiveness for holding the dressing in place, the presence of the exudate on the wound is conducive to bacterial infection. For these primary reasons, it is well known to provide various reservoirs including plain gauze sponges, absorbent pads, hydrogel or other hydrocolloid materials and the like to retain wound exudate.

It is also known in the art to provide a bacterial barrier cover for the dressing.

As heretofore alluded to, U.S. Pat. No. 4,499,896 issued to Heinecke describes an embodiment of a dressing wherein an absorbent fabric reservoir for retaining wound fluid is provided with a cover that is a barrier to bacteria and/or other external contaminants.

However, the patented dressing contains no means for removal of air entrained within the interstices or voids of the fabric reservoir. Since removal or displacement of this entrained air is necessary to free these interstices to act as a sponge for retention of wound fluid diffusing thereto, it follows that the capacity of the patented dressing for receiving wound exudate is appreciably less than its potential.

A primary task of this invention accordingly may be said to be to improve over the teachings of the Heinicke patent and provide a wound dressing having an absorbent pad or fabric reservoir for receiving and retaining wound exudate, which dressing provides a complete barrier to bacteria and/or other external contaminants while at the same time optimizing the ability of the fabric reservoir to wick, i.e. receive wound fluid.

This task is accomplished by providing the barrier with means permitting egress of air entrained in the fabric reservoir to the atmosphere, which entrained air will prevent optimum wicking of the wound fluid. In other words, it is axiomatic that for one fluid to be able to diffuse or wick to a given volume of space, any fluid (e.g. air) initially present therein must first be permitted to be displaced.

The nature and objects of the invention may best be understood by reference to the accompanying illustrative drawing taken in conjunction with the following detailed description.

As shown therein, the novel dressing 10 of this invention comprises a bottom thin sheet or film 12 adapted for placement on the skin over the wound (not shown). Film 12 is shown to have a plurality of perforations 14 permitting passage of the wound fluid therethrough to a porous fabric reservoir 20.

Reservoir 20 is shown to be covered with a liquid-and bacteria-impermeable sheet 16. Sheet 16 and film 12 are sealed in liquid-and bacteria-tight relationship around their common periphery so that exudate cannot escape through the edges of the dressing, nor can any external contaminants, including bacteria, enter into the dressing and then pass through the porous film 12 to the underlying wound.

As shown, the outer cover is provided with one or more windows or openings 16a to permit egress of air from the interstices of reservoir 20. Each such window or opening is shown to be covered by an air-permeable bacterial barrier sheet material 18 of slightly larger dimensions than the dimensions of opening 16a. As illustrated, sheet 18 is sealed around its periphery to the edges of sheet 16 around opening 16a so as to prevent ingress of bacteria around the edges of the opening.

In order to secure the dressing to the skin, and to maintain the barrier function of the dressing against bacteria and other external contaminants, pressure-sensitive adhesive coating 22 is provided around the entire periphery of film 12.

It will be appreciated that the adhesive coating 22 may and typically will be initially covered with a suitable release sheet or sheets to prevent premature contact of the adhesive prior to application of the dressing. Most preferably, the release sheet will be impermeable to bacteria to provide the additional function of maintaining the contaminant-free environment of the dressing during its shelf life and prior to application over a wound.

The particular materials employed for preparing the various components of the dressing may be selected from those heretofore known in the art for providing their respective functions. Since such materials are well known and their selection will be a matter of choice within the expected judgement of the skilled worker in the light of the foregoing description, their selection per se accordingly comprises no part of this invention.

However, by way of further illustration, film or sheet 12 may comprises any of the known perforated films adapted for placement on a wound surface and may be on the order of one mil thick. As examples of such films, mention may be made of polyurethane, cellulose acetate, cellulose triacetate, etc. While for purposes of illustration, film or sheet 12 has been shown to be perforated, it will be appreciated that where found desirable or expedient, to do so, suitable porous materials such as cellulose esters and the like may be employed in lieu thereof, including porous sheet materials which have been chemically treated or coated to make them more suitable for applying to the wound. Since the desired degree of porosity or permeability to wound exudate will vary according to such factors as the nature of the intended wound to be covered, the anticipated amount of exudate and/or the frequency of dressing changes contemplated, it is not susceptible to precise quantification. In an event, the selection of the particular permeability to wound exudate for a given dressing will be a matter of choice of design without the judgement of the skilled worker in the light of this description. As will be appreciated, the particular material selected for film 12 should be "wound friendly", i.e. a material that is innocuous with respect to the healing wound and easily removable with minimal damage or insult to the healing skin.

Water-impermeable sheet 16 should of course also be impermeable to bacteria as well. It may, for example be on the order of 0.5 to 1.0 mil thick and comprise a suitable polymeric material such as polyurethane, "Saran" (trademark of Dow Chemical), a polyolefin such as polyethylene or polypropylene, a polyester such as polyethylene terephthalate, etc. In any event, sheet 16 must be imperforate as well as being flexible and conformable.

Bacterial barrier 18 may comprise any of the per se known bacterial barrier air filters such as NUCLEOPORE, MILLIPORE, GELLMAN, etc.

Reservoir 20 may comprise any of the fabric materials heretofore employed for wound dressings to retain exudate, e.g. cotton, gauze sponges, absorbent pads such as those customarily used for abdominal surgery, and the like. If desired, they may additional contain an antimicrobial agent such as chlorhexidine, although the use of such a reagent is not considered necessary.

The adhesive employed around the periphery of bottom sheet 12 may be any of the known so-called medical grade adhesives heretofore employed for application to the skin. Such known adhesives include the rubber-based, acrylic, vinyl ether and hydrocolloid pressure-sensitive adhesives. It will of course be understood that in order to provide the bacterial barrier critical to the practice of this invention, the selected adhesive must be applied as a continuous layer around the periphery of the bottom sheet.

As the particular materials selected per se comprise no part of this invention, in like manner it is not material to the practice of this invention how sheet 16 is secured in the described manner to sheet 18 and/or film 12. They may, for example, be secured in bacteria-tight relationship by heat sealing or by means of a suitable heat- or pressure-sensitive adhesive.

It is to be expressly understood that the wound dressing shown in the illustrate drawing is capable of various modifications without departing from the scope of the invention herein contemplated.

For example, since the bacterial barrier sheets are relatively expensive, the cover for the dressing has been shown to consist essentially of a conventional impermeable sheet material provided with an opening or window which is covered by the relatively more expensive bacterial barrier sheet. However, it is contemplated that the cover may instead comprise a single air-permeable, bacteria- and liquid-impermeable sheet material. Embodiments are also contemplated wherein the dressing does not have a perforate bottom sheet and, in lieu thereof, the absorbent pad is attached to the outer cover, e.g. by spot sealing. In such embodiments, the bottom sheet is not needed and the adhesive coating for securing the bandage and will instead be situated around the periphery of the cover sheet.

Other changes will be readily suggested in the light of the foregoing description.

By way of recapitulation, it will be seen that the present invention provides a wound dressing having a fabric reservoir for receiving and retaining wound fluids, the reservoir being encased within outer walls which provide an effective barrier to external contaminants while at the same time permitting egress of air from within the interstices or voids of the fabric reservoir in order to optimize the amount of wound fluid which can be wicked into the fabric reservoir. This optimizing of wicking in turn minimizes the frequency of dressing changes which may be required.

Since it is not possible to ascertain whether the bacterial barrier precludes the presence of any bacteria within the reservoir so that it can be said to be totally bacteria-free, as used herein and in the appended claims, the term "effective barrier" is used, denoting a barrier which "effectively" precludes ingress of bacteria from the ambient atmosphere to the reservoir, whereby the reservoir and the chamber in which it is contained can be reasonably regarded as being safe from the danger of infection induced by the presence of bacteria entering the dressing from the ambient atmosphere.

Since certain changes may be made without departing from the scope of the invention herein contemplated, all matter contained in the foregoing description and drawing shall be taken as being illustrative and not in a limiting sense.

What is claimed is:

1. In a wound dressing including a fabric reservoir for receiving and retaining wound fluids;

the improvement wherein said dressing is provided with an outer cover characterized as being an effective bacterial barrier, at least a portion of said cover further being characterized as being air permeable, the periphery of a surface of said dressing containing a continuous layer of a pressure-sensitive adhesive for securing said dressing to skin, said adhesive layer further serving to provide a bacterial barrier.

2. A wound dressing as defined in claim 1 wherein said cover comprises a liquid-impermeable first sheet material having at least one window through which air can pass, each said window being covered by a second sheet material of slightly larger dimensions than said window, said first sheet material and each said second sheet material being sealed together to provide a bacterial barrier around the periphery of each said window, each said second sheet material comprising an air-permeable bacterial barrier.

3. A wound dressing including a reservoir for receiving and retaining wound fluids, said dressing comprising:

(1) a bottom sheet material permeable to wound fluids adapted for placement on the skin over a wound;

(2) an outer cover characterized as being a bacterial barrier, at least a portion of said cover further being characterized as being air permeable, said outer cover and bottom sheet material being sealed together around their common periphery in spaced relationship to define a chamber therebetween for receiving wound fluids diffusing through said bottom sheet material, said seal providing a barrier against ingress into said chamber of bacteria or other external contaminants; and (3) a fabric material disposed within said chamber, said fabric material having voids or interstices providing said reservoir for receiving and retaining said wound fluids, the air permeability of said cover being sufficient to permit egress of air from said voids within said reservoir to optimize the amount of fluids said reservoir can receive by diffusion through said bottom sheet material, the bacterial barrier provided by said cover and the seal of said cover to said bottom sheet material cooperating to provide an effectively contaminant-free environment within said chamber;

said cover comprising a liquid-impermeable first sheet material having at least one window through which air can pass, each said window being covered by a second sheet material of slightly larger dimensions than said window, said first sheet material and each said second sheet material being sealed together to provide a bacterial barrier around the periphery of each said window, each said second sheet material comprising an air-permeable bacterial barrier.

4. A wound dressing as defined in claim 3 wherein the periphery of the surface of said bottom sheet material opposed from the surface sealed to said cover contains a continuous layer of an imperforate pressure-sensitive adhesive for securing said dressing to the skin, said adhesive layer further serving to provide a bacterial barrier.

5. A wound dressing as defined in claim 4 further including a release sheet covering said adhesive layer and said opposed surface of said bottom sheet material.

6. A wound dressing as defined in claim 5 wherein said bottom sheet material comprises a substantially liquid-impermeable material, said sheet material having a plurality of perforations permitting passage of wound fluid therethrough.

7. A wound dressing as defined in claim 3 wherein said fabric material reservoir is in the form of a pad or sponge.

8. A wound dressing including a fabric reservoir having voids for receiving and retaining wound fluids therein, said reservoir being characterized as being contained in a contaminant-free environment permitting egress of air from said voids, said wound dressing comprising:

a bottom sheet material adapted for placement on the skin to cover a wound, said bottom sheet material being permeable to wound fluids and having a continuous, imperforate layer of a pressure-sensitive adhesive around the entire periphery of one surface thereof whereby to permit securing of said bottom sheet material to the skin surrounding the wound in an effectively bacteria-tight relationship;

a cover sheet material characterized as being a bacterial barrier, said cover sheet material being further characterized as being air-impermeable, said cover sheet material having a window between its borders through which air can pass, said cover sheet material and said bottom sheet material being sealed together around their common periphery in spaced relationship to define a chamber therebetween for receiving wound fluids diffusing through said bottom sheet material to said chamber;

a bacterial barrier sheet material covering said window and secured around its periphery to said cover sheet material whereby to provide an effective barrier against ingress of bacteria through said window in said cover sheet material, said bacterial barrier sheet material being air-permeable whereby to permit egress of air from within said chamber through said window to the ambient atmosphere; and said fabric reservoir contained in said chamber.

9. A wound dressing as defined in claim 8 wherein said fluid permeability of said bottom sheet material is provided by a plurality of perforations in said bottom sheet material.

10. A wound dressing as defined in claim 8 wherein said fabric reservoir is in the form of a pad or sponge.

* * * * *